United States Patent [19]

Davis

[11] Patent Number: 4,723,030

[45] Date of Patent: Feb. 2, 1988

[54] MODERATED REDUCTION REACTIONS FOR PRODUCING ARYLHYDROXYLAMINES

[75] Inventor: Gary C. Davis, Albany, N.Y.

[73] Assignee: General Electric Company, Schenectady, N.Y.

[21] Appl. No.: 762,358

[22] Filed: Aug. 5, 1985

[51] Int. Cl.$^4$ .................... C07C 83/00; C07C 101/00
[52] U.S. Cl. ........................................ 560/19; 560/20; 564/300; 564/418; 564/423
[58] Field of Search ................. 560/15; 564/300, 423, 564/418

[56] References Cited

U.S. PATENT DOCUMENTS

| | | | |
|---|---|---|---|
| 3,694,509 | 9/1972 | Rylander et al. | 360/578 |
| 3,715,397 | 2/1973 | Rylander et al. | 260/575 |
| 3,927,101 | 12/1975 | Ludec | 260/580 |
| 3,992,395 | 11/1976 | Ludec | 260/307 A |
| 4,571,437 | 2/1986 | Caskey et al. | 564/418 |

FOREIGN PATENT DOCUMENTS

| | | | |
|---|---|---|---|
| 0086363 | 8/1983 | European Pat. Off. | 564/300 |
| 54-24837 | 2/1979 | Japan. | |
| 1388523 | 5/1972 | United Kingdom. | |

OTHER PUBLICATIONS

Makaryan et al., Izvestiva Akademii Nauk SSSR, No. 4, pp. 750–764 (Apr. 1983), original article submitted Mar. 17, 1982.

*Primary Examiner*—Robert V. Hines
*Attorney, Agent, or Firm*—Francis T. Coppa; James C. Davis, Jr.; James Magee, Jr.

[57] ABSTRACT

A method is provided for enhancing the production rate of arylhydroxylamines by moderated catalytic hydrogenation reactions. Small quantities of acid introduced to the reaction medium doubles the hydrogenation rate of nitroaromatic compounds without a significant loss in selectivity to arylhydroxylamines.

18 Claims, No Drawings

MODERATED REDUCTION REACTIONS FOR PRODUCING ARYLHYDROXYLAMINES

BACKGROUND OF THE INVENTION

This invention is related to the production of arylhydroxylamines from nitroaromatic compounds. More particularly, it is directed to methods for rapidly producing such arylhydroxylamines in high yields without producing large quantities of coproducts, such as aniline.

Arylhydroxylamines are precursors in the synthesis of diarylnitrones. Certain diarylnitrones have been found to be useful in contrast enhancement photolithography. Methods for the production of these diarylnitrones and their use are more particularly described in copending applications Ser. Nos. 735,016, 675,915, 676,918 and 687,681, all assigned to the same assignee as the present invention. The contents of these copending applications are incorporated herein by reference. The arylhydroxylamines provide arylnitrones typically by reaction with an aldehyde, preferably arylaldehydes.

These arylhydroxylamines are prepared by the reduction of nitroaromatic compounds. Reduction of nitroaromatics has been accomplished by metal reductions, electrochemical reductions and catalytic hydrogenation reactions. Electrochemical reductions are very costly and therefore, are not preferred. Metal reductions are effective but pose problems in waste disposal and in overreducing the nitroaromatics to aromatic amines. Catalytic hydrogenation is a very attractive scheme, however, over reduction to aromatic amines is also a problem. Rylander et al., U.S. Pat. No. 3,694,509, discloses a catalytic hydrogenation reaction which is moderated to prevent overreduction of the nitroaromatics. Rylander et al. utilizes a precious metal catalyst in neutral media and the moderator dimethylsulfoxide (DMSO) to produce N-arylhydroxylamines. Other moderated reduction reactions have been disclosed such as the divalent sulphur compounds of Caskey et al. U.S. Pat. No. 4,415,753; tetravalent sulfoxides, U.S. Pat. No. 3,897,499; organic bases, U.S. Pat. Nos. 3,927,101 and 3,992,395 and the phosphorus compounds disclosed in Japanese Pat. No. 54[1979]-24837. Although these moderated reactions are selective in producing arylhydroxylamines, there remains room for improvement. Selectivity is obtained in these reactions by depressing the rate of reduction. As a result, these reactions are relatively slow when compared to unmoderated reactions. It is desirable to enhance the rate of reduction in these reactions without losing selectivity.

The addition of acid to an unmoderated reduction reaction has been shown to have no catalytic effect by Makaryan et al. in Investiya Akademii Nauk SSSR, No. 4, pp. 750-764, (April, 1983) as translated by the Academy of Sciences of the USSR, 692-695 (1983). Rylander (U.S. Pat. No. 3,715,397) has shown that the reduction of nitroaromatics in aqueous solutions of 25% sulfuric acid, in the presence of the moderator DMSO, results in aminophenol rearrangement products.

The principal object of the present invention, therefore, is to provide moderated catalytic hydrogenation reactions wherein the nitroaromatic compounds are not overreduced. Another object of the present invention is to enhance the rate of reduction of nitroaromatics and increase the yield of arylhydroxylamines from moderated reactions without a loss in selectivity and without producing rearrangement products. Other objects will be obvious from the discussions herein.

DETAILED DESCRIPTION OF THE PREFERRED EMBODIMENTS

The present invention is based on the discovery that moderated catalytic hydrogenation reactions of nitroaromatic compounds can be further catalyzed with acid to provide higher reduction rates without rearrangement and without a significant loss in arylhydroxylamine selectivity. Furthermore, it has been found that yields obtained from such reactions are dependent upon the solvents utilized.

The nitroaromatics which can be reduced to the corresponding arylhydroxylamines are those having an aromatic nucleus of from about 6 to 30 carbon atoms. These aromatic nucleii may contain substituents such as halogen, cyano groups, alkyl radicals ($C_{1-8}$), substituted alkyl radicals ($C_{1-8}$), aliphatic acyl radicals ($C_{1-8}$), aryl radicals ($C_{6-13}$), substituted aryl radicals ($C_{6-13}$) and alkoxy carbonyl radicals ($C_{1-8}$). As many as five of such substituents may appear on the aromatic nuclei. As many as two nitro groups may appear on each aromatic nuclei of these nitroaromatic compounds. The preferred nitroaromatics have only one aromatic nucleus with only one nitro group.

Those nitroaromatics which can be conveniently reduced to the arylhydroxylamines are those having a phenyl aromatic nucleus. These arylhydroxylamines are particularly useful in producing the diarylnitrones used in photolithography. The preferred nitroaromatic compounds which generate such materials include nitrobenzene, 4-chloro nitrobenzene, 3,4-dichloronitrobenzene, 4-carboethoxy nitrobenzene, 4-acetylnitrobenzene and 4-cyanonitrobenzene. Others include 4-nitrotoluene, 3-nitroethylbenzene, 2-methyl-4-nitrotoluene, 3-chloronitrobenzene, 4-fluoronitrobenzene, 5-chloro-1-nitrophthalene, 3-nitro-1-phenylethanol, 4-nitro-2-phenylethanol, 4-nitrophenol, 2-nitroanisole, 4-aminonitrobenzene and 3-nitrobenzonitrile and the like.

The noble metal hydrogenation catalysts utilized in this invention are those which are generally known to provide arylhydroxylamine selectivity when used with moderators. A wide variety of noble metal catalysts are suitable which include, but are not limited to, palladium, platinum, ruthenium, iridium, rhodium, osmium, rhenium, and the like, including the oxides thereof. The rates of hydrogenation are known to vary with the metal and type of catalyst utilized including the support utilized. Metals supported on carbon are generally preferred with platinum-on-carbon being most preferred. Any amount of catalyst effective for nitroaromatic hydrogenation is suitable for use in this invention, however, high concentrations of catalysts are undesirable in that they encourage overreduction to aromatic amines. Preferred carbon supported catalysts contain up to 35% noble metal, with concentrations of from 2 to 10% noble metal being most preferred. Weight ratios of starting material to catalyst preferably fall within the range of about 100:0.1-5.

The moderators suitable for use in this invention are those compounds known to enhance the selectivity of nitroaromatic hydrogenation products to the arylhydroxylamines. These include heterocyclic nitrogen compounds, phosphines, phosphites, sulfides (divalent sulphur) and sulfoxides (tetravalent sulphur). Suitable heterocyclic nitrocompounds include pyridine, quinoline, piperidine, pyrolidine, pyrrole, and the like. Also included are the alkylated species (C$_{1-4}$) of these nitrogen heterocycles having from 1 to 2 alkyl substituents including N-butylpiperidine, N-ethylpiperidine, N-methylpiperidine, 1,2-dimethylpiperidine, 1-ethyl-2-methylpiperidine, N-methylpyrrolidine, 2-ethylpyrrolidine, N-butylpyrrolidine, 1-ethyl-2-methylpyrrolidine, 1,2-dimethylpyrrolidine, 2-methylpyridine, 3-methylpyridine, 4-methylpyridine, 2-ethylpyridine, 3-ethylpyridine, 4-ethylpyridine, 2-(or 3-)(or 4-) butylpyridine, 2,3-dimethylpyridine, 2,5-dimethylpyridine, 3-ethyl-5-methylpyridine, 3-ethyl-6-methyl-1-pyridine, and the like. Those disclosed by Ludec et al. in U.S. Pat. Nos. 3,992,395 and 3,927,101 are also suitable, the contents of which are incorporated herein by reference.

Suitable sulfides are those of the general formula R$_2$S wherein R is selected from the group consisting of alkyl radicals of from 1 to 18 carbon atoms, aromatic radicals of from 6 to 20 carbon atoms, substituted alkyl radicals of from 1 to 18 carbon atoms and substituted aromatic radicals of from 6 to 20 carbon atoms. These divalent sulfur compounds are more particularly described by Reed in *Organic Chemistry or Bivalent Sulfur*, Vol. II, (1960), pp. 17–58, 305–374 and 105–133. A particularly preferred bivalent sulfur compound is dimethylsulfide.

Suitable sulfoxides are those of the formula R$_2$S=O, wherein R is as previously defined. Particular sulfoxides include dimethylsulfoxide, diethylsulfoxide, di-N-propylsulfoxide, di-N-butylsulfoxide, diisoamylsulfoxide, benzylphenylsulfoxide, diphenylsulfoxide, phenylmethylsulfoxide, dibenzylsulfoxide, di-p-tolylsulfoxide, phenyl-tolylsulfoxide, ditolylsulfoxide, and the like. Of the sulfoxides, dimethylsulfoxide is the most preferred.

The phosphines and phosphites which have been found to function as moderators include those of the formulas R'$_3$P and P(OR')$_3$ wherein R' is selected from the group consisting of alkyl radicals of from 1 to 18 carbon atoms, alkoxy radicals of from 1 to 18 carbon atoms, aryl radicals of from 6 to 20 carbon atoms and the substituted derivatives of the alkyl, alkoxy and aryl radicals within this group. Particular phosphines and phosphites include triphenylphosphine, trioctylphosphine, triethylphosphine, trimethylphosphine, trimethoxyphosphine, triethoxyphosphine, triphenoxyphosphine, tributylphosphine, methylphosphine, ethylphosphine, N-butylphosphine, isobutylphosphine, t-butylphosphine, 2-hydroxyethylphosphine, phenylphosphine, dimethylphosphine, diethylphosphine, diphenylphosphine, and the like. The preferred phosphines are triphenylphosphine and trioctylphosphine.

The amount of moderator used in the process of this invention is that which is effective for enhancing the selectivity of the hydrogenation reaction to arylhydroxylamines. The quantity of moderator utilized should correspond to the quantity of metal catalyst. Molar proportions of metal catalysts to moderator preferably fall within the range of about 1:0.5 to 5 and most preferably range from about 1:1 to 2. It is preferable to utilize small quantities of moderators so as to facilitate separation from the arylhydroxylamine in subsequent processing. For this reason, phosphines such as trioctyl phosphine and triphenylphosphine are preferred for their effectiveness at low concentrations. Weight ratios of starting material to moderator within the range of 100:0.5 to 75 are typical. However, ratios of 100:0.5 to 2 are preferred.

The moderator utilized may be complexed with the metal catalyst prior to use in the reaction, thus generating a homogeneous catalyst species. However, separately adding the moderator and catalyst to the reaction mixture has been found to be more convenient.

To enhance the rate of hydrogenation in accordance with this invention, an acid is introduced into the moderated reduction reaction. Essentially any protonic acid is suitable for enhancing the rate of reaction. The term "protonic acid" as used herein is intended to describe compounds which dissociate in water and provide a free proton to form H$_3$O$^+$. These include both mineral acids and organic acids. Particularly suitable are the strong mineral acids, such as the hydrogen halides and the oxo-acids of sulphur, phosphorous and nitrogen. Hydrogen halide acids such as hydrogen chloride, hydrogen bromide, hydrogen fluoride, perchloric, and the like, all will enhance the rate of reduction for a moderated catalytic system. Suitable phosphorus oxide acids include phosphorus acid, phosphoric acid and the like. Suitable sulfur oxide acids include sulfurous (H$_2$SO$_3$), sulfuric (H$_2$SO$_4$), and the like. Another suitable mineral acid is nitric acid (HNO$_3$).

Also suitable are the strong organic acids, such as sulfonic acids and strong carboxylic acids. The term "strong carboxylic acid", as used herein, is intended to include carboxylic acids having dissociation constant values which approach or exceed that of acetic acid. Particular examples of suitable carboxylic acids include, acetic acid, formic acid, propanoic acid, butanoic acid, 2-methylpropanoic acid, pentanoic acid, hexanoic, heptanoic, chloroacetic acid, trichloroacetic acid, trifluroacetic acid, phenylacetic acid, 2-chlorobutanoic acid, 3-chlorobutanoic acid, dichloroacetic acid, 4-chlorobutanoic acid, 5-chlorobutanoic acid, and the like. The sulfonoic acids are preferred and include methanesulfonic acid, ethylsulfonic acid, phenylsulfonic acid, butylsulfonic acid, and the like.

Also included within the suitable acids are the acid functionalized polymer resins such as that under the trade name Amberlyst XN-1005 produced by Rohm and Haas Co. These acids are convenient in that they remain a solid and can be easily removed from a reaction mixture. These resins are typically functionalized with carboxylic acid or sulfonic acid groups.

Stronger acids provide the fastest rates and they are typically preferred because of this feature. A typical example is methanesulfonic acid or the Amberlyst XN-1005 resin.

Small quantities of acid must be used to prevent rearrangement to aminophenols. Quantities of acid which provide 0.01 to 10 weight percent of solution have been found to be suitable. However, concentrations both above and below this range are expected to be suitable, depending on the strength of the acid.

Reaction in the liquid phase is preferred. Suitable solvents include lower aliphatic alcohols such as methanol, ethanol, isopropanol, propanol, n-butanol, t-butanol, liquid hydrocarbons such as benzene, hexane, heptane, cyclohexane, toluene, octane, xylene, and the like. Water may also be used, however, rearrangement can occur where stronger acids are used. Preferred solvents are lower aliphatic alcohols, particularly ethanol. The concentration of solvent can vary widely. Preferred concentrations fall within the range of about 10 to 75% by weight of the reaction medium.

The yield of arylhydroxylamine obtained from the hydrogenation reaction has been found to be dependent upon the solvent utilized in the reaction. Those solvents which have been found to give good yields include oxygenated solvents, such as lower aliphatic alcohols, ethers and ketones. Alcohols are most preferred. Nonoxygenated, highly polar solvents are also suitable, provided they do not poison the catalyst. Adding a small quantity of a highly polar solvent, such as diglyme, will improve the performance of the reaction within a poor solvent, such as toluene. Particularly good solvents are ethanol, methanol, diethylether, acetic acid, dimethoxyethane, dioxane, diglyme, acetone and acetonitrile. Poor solvents have been found to include toluene, chloroform, N-methylpyrrolidone, formamide and water. The reagents of these reactions must be soluble in the solvents selected for optimum rate and yield of arylhydroxylamine. However, the reagents need only be partially soluble in the solvent selected to provide the desired results of this invention.

The hydrogenation reaction can be performed within a temperature range of about $-50°$ C. to $150°$ C., preferably $0°$ to $50°$ C., and most preferably at ambient temperature. In addition, the pressure can range from about 0.1 atmospheres to 100 atmospheres with operation at 1 atmosphere hydrogen often being preferred. Higher temperatures and pressures provide greater reaction rates, however, a loss in selectivity also results. Operation at temperatures and pressures near ambient conditions are often economical and convenient. Hydrogenation will proceed until about 2 molar equivalents of hydrogen are absorbed by the system.

Hydrogenation can be accomplished in conventional equipment either batchwise or continuously. The hydrogen feed is typically stopped after 2 molar equivalents are absorbed, wherein the catalyst is removed and the product is recovered from solution by conventional means such as precipitation and filtration.

The following examples are provided to illustrate the invention. It is not intended to limit the scope of this invention to the embodiments described herein.

The following experimental procedure was followed for Examples 1-10.

Into an atmospheric hydrogenator were added 10 millimoles of a nitroaromatic as indicated in the corresponding example, 0.55 gms dimethylsulfoxide (DMSO), 50 mg of a 5% platinum-on-carbon catalyst, 10 cc of absolute ethanol and, where used, an acid catalyst in a quantity more particularly described in the examples below. The system was charged with hydrogen and stirred at room temperature ($20°$ to $25°$ C.) until 2 equivalents of hydrogen had reacted. The reaction mixture was then analyzed by liquid chromatography to determine the composition of the reaction mixture.

EXAMPLES 1-2

The nitroaromatic compound utilized was p-nitroethylbenzoate (1.95 gms) and the acid introduced was methanesulfonic acid in the concentration indicated within Table I below. Liquid chromatograph analysis of the reaction products and the rate of reaction is shown in Table I below.

TABLE I

| | Methanesulfonic Acid Catalysts | | | |
|---|---|---|---|---|
| Run | Acid** | DMSO (gms) | $H_2$ Rate (cc/min) | Ratio (PHA/A)* |
| Example 1 | 0.20 gms | 0.55 | 8.2 | 97:3 |
| Example 2 | 0.01 ml | 0.55 | 8.1 | 96:3 |
| Control A | none | 0.55 | 5.4 | 96:2 |
| Control B | none | none | 10.8 | 38:41 |

*PHA = p-hydroxylamine ethylbenzoate
A = p-aminoethylbenzoate
**Acid = methanesulfonic acid The above results show the small quantities of strong acid necessary to significantly enhance the rate of hydrogenation. The absence of a moderator/acid combination is deleterious to either the rate of reaction or its selectivity.

EXAMPLE 3

Three runs were made utilizing nitroethylbenzoate (1.95 gms). The initial run did not contain any acid while the second and third run contained 0.5 cc of acetic acid. The third run utilized acetic acid without the dimethyl sulfoxide moderator. The products were analyzed by liquid chromatography, the results of which are shown in Table II along with the rate at which hydrogen was consumed.

TABLE II

| | Acetic Acid Catalyst | | | |
|---|---|---|---|---|
| Run | Acetic Acid | DMSO (gms) | $H_2$ Rate (cc/min) | Ratio (PHA/A)* |
| 1 | none | 0.55 | 5.4 | 94:2 |
| 2 | 0.5 cc | 0.55 | 5.9 | 93:1 |
| 3 | 0.5 cc | none | 9.7 | 38:39 |

*As indicated in Table I

The results of Example 3 show a smaller enhancement in yield where a weaker acid (acetic acid) is introduced to the moderated hydrogenation reaction. In addition, these results show that where the moderator/acid cobmination is not used, either the rate of reaction or its selectivity suffers.

EXAMPLES 4-9

In Examples 4-9 the nitroaromatic compound hydrogenerated was p-nitroethylbenzoate (1.95 gms) and the acid utilized was the acid functionalized resin Amberlyst XN-1005 (4 meq $H^+$/gm). This Amberlyst Resin is sold by Rohm & Haas Co. and is believed to be a sulfonated polystyrene resin. The quantity of Amerlyst Resin utilized in Examples 4-10 and the rates of reaction obtained therefrom are shown in Table III along with the results of liquid chromatograph analysis of the reaction products.

TABLE III

| | Amberlyst XN-1005 Resin Catalysts | | | |
|---|---|---|---|---|
| Run | Acid** (gm) | DMSO (gm) | $H_2$-Rate (cc/min) | Ratio (PHA/A)* |
| Example 4 | 1.0 | 0.55 | 8.8 | 99:1 |
| Example 5 | 0.50 | 0.55 | 7.4 | 99:1 |
| Example 6 | 0.25 | 0.55 | 7.5 | 98:2 |
| Example 7 | 0.10 | 0.55 | 7.7 | 98:1 |
| Example 8 | 0.05 | 0.55 | 7.3 | 97:2 |
| Example 9 | 0.005 | 0.55 | 7.7 | 98:2 |
| Control A | none | 0.55 | 5.4 | 96:2 |
| Control B | none | none | 10.1 | 38:41 |
| Control C | 0.5 | none | 12.8 | 57:26 |

*As indicated in Table I
**Acid = Amberlyst XN-1005 Resin

The results within Table III illustrate the small quantity of catalyst necessary to obtain the desired rate enhancement. For example, decreasing the quantity of acid by two orders of magnitude does not significantly affect the rate of reaction.

EXAMPLES 10-12

For Examples 10-12 p-nitroethylbenzoate (1.95 gms) was hydrogenated with the use of trifluroacetic acid. The quantity of trifluroacetic acid utilized is indicated in Table IV along with the corresponding hydrogenation rate and the liquid chromatograph analysis of the reaction products.

TABLE IV

| | Trifluoroacetic Acid Catalyst | | | |
|---|---|---|---|---|
| Run | Acid** (mmoles) | DMSO (gm) | $H_2$-Rate (cc/min) | Ratio (PHA/A)* |
| Example 10 | 10 | 0.5 | 11.1 | 96:3 |
| Example 11 | 2 | 0.5 | 8.3 | 97:3 |
| Example 12 | 0.2 | 0.5 | 8.9 | 97:2 |
| Control A | none | 0.5 | 5.4 | 96:2 |
| Control B | none | none | 10.1 | 38:41 |

*As indicated in Table I
**Acid = trifluoracetic acid

The Examples above illustrate that the rates of reaction can be more than doubled without significantly affecting selectivity to arylhydroxylamine.

EXAMPLE 13

In this Example the moderator hydrogenation reaction was run with various solvents. In each of the runs described below 1.95 gms of p-nitroethylbenzoate, 0.55 gms dimethylsulfoxide, 50 mg of 5% platinum on carbon and 10 cc of solvent were utilized. The system was charged with hydrogen and stirred at room temperature (about 20° to 25° C.) and the hydrogen uptake was monitored. The reaction mixtures were analyzed by liquid chromatography to determine the effects of solvents on the reduction. Results are shown in Table V.

TABLE V

| Effect of Solvents on Modified Hydrogenation | | |
|---|---|---|
| Solvent | $H_2$-Rate (cc/min) | Ratio PHA/A/H*** |
| Ethanol | 5.4 | 94:2:1 |
| Toluene | 3.2 | 86:11:2 |
| Chloroform | 4.2 | 62:21:>1 |
| Water | 0.5 | 41:43:>1 |
| Formamide | 0* | 0 |
| Acetonitrile** | 4.7 | 99:1:>1 |
| Diethylether | 3.2 | 96:2:2 |
| Dimethoxyethane | 3.7 | 94:1:>1 |
| Dioxane | 0.9 | 92:3:>1 |
| Diglyme | 2.6 | 99:>1:>1 |
| Acetone | 3.2 | 98:2:>1 |
| Acetic Acid | 5.1 | 69:17:1 |
| Toluene/0.5 cc Dyglyme | 2.3 | 89:1:>1 |

*Catalyst poisoned
**0.5 gms Amberlyst XN-1005 Resin also introduced
***PHA - as indicated in Table I
A - as indicated in Table I
H - hydrazo compound The results of Table V illustrate the effects various solvents have on the rate of reduction and the selectivity.

The Examples above illustrate particular embodiments of this invention. Variations will be obvious to those skilled in the art and are considered within the scope of this invention.

What is claimed is:

1. A method for producing arylhydroxylamines comprising reducing a nitroaromatic compound within a solution with hydrogen at a temperature in the range of −50° C. to 150° C. and a pressure of from about 0.1 atmosphere to about 100 atmospheres, in the presence of an effective amount of a noble metal hydrogenation catalyst and a reaction moderator, said solution comprising a protonic acid in an amount which is sufficient to accelerate the hydrogenation reaction but insufficient to cause the rearrangement of the arylhydroxylamine to an aminophenol.

2. A method as in claim 1 wherein the noble metal is selected from the group consisting of platinum, rhenium, rhodium, palladium and nickel.

3. A method as in claim 1 wherein the noble metal catalyst is platinum-on-carbon.

4. A method as in claim 3 wherein the platinum-on-carbon catalyst contains 2-10% platinum.

5. A method as in claim 1 wherein the reaction moderator is selected from the group of compounds consisting of phosphines, phosphites, sulfides, sulfoxides and heterocyclic nitrogen compounds.

6. A method as in claim 1 wherein the reaction moderator is selected from the group consisting of triphenyl phosphine, trioctylphosphine, triphenylphosphite, dimethylsulfide, piperidine, pyrrole, pyrrolidene, quinoline, pyridine and dimethylsulfoxide.

7. A method as in claim 1 wherein the nitroaromatic compound has an aromatic nucleus of from 6 to 30 carbon atoms with from one to two nitro groups and from 0 to 5 substituents selected from the group consisting of alkyl radicals of from 1 to 8 carbon atoms, substituted alkyl radicals of from 1 to 8 carbon atoms, aryl radicals of from 6 to 13 carbon atoms, substituted aryl radicals of from 6 to 13 carbon atoms, aliphatic acyl radicals of from 1 to 8 carbon atoms, alkoxy-carbonyl radicals of from 1 to 8 carbon atoms and halogen.

8. A method as in claim 1 wherein the nitroaromatic compound is selected from the group consisting of nitrobenzene, p-ethoxynitrobenzene, p-nitroethylbenzoate and p-nitromethylbenzoate.

9. A method as in claim 1 wherein the acid is selected from the group consisting of hydrogen chloride, hydrogen bromide, hydrogen fluoride, perchloric, acetic, formic, propanoic, butanoic, pentanoic, hexanoic, heptanoic, 2-methylpropanoic, chloroacetic, trichloroacetic, trifluoroacetic, phenylacetic, phosphoric, phosphorus, sulfurous, sulfuric, and nitric.

10. A method as in claim 1 wherein the acid within the solution is selected from the group consisting of acetic acid, methanesulfonic acid, trifluroacetic acid and trichloroacetic acid.

11. A method as in claim 1 wherein the acid within the solution is in the form of an acid functionalized polymer resin.

12. A method as in claim 10 wherein the polymer resin is a sulfonic acid substituted polystyrene resin.

13. A method as in claim 12 wherein the quantity of acid utilized falls within the range of 0.01 to 0.05 weight percent of solution.

14. The method of claim 1 wherein the protonic acid constitutes about 0.01 to about 10 weight % of the solution.

15. A method as in claim 1 wherein the solvent forming said solution is selected from the class consisting of alcohols, esters and ketones.

16. A method as in claim 15 wherein the solvent is selected from the group consisting of ethanol, diglyme, acetic acid and acetone.

17. A method for producing arylhydroxylamines which comprises reducing nitroaromatic compounds of from 6 to 20 carbon atoms having from 1 to 2 nitro groups within an acidic ethanol solution with hydrogen at a temperature in the range of $-50°$ C. to $100°$ C. and a pressure of about 1 atmosphere in the presence of a 2-10% platinum-on-carbon catalyst and a reaction moderator selected from the group consisting of dimethylsulfide, triarylphosphine, triethylphosphine, piperidine and quinoline, said acidic solution having from 10 to 0.05 weight percent acid, said acid being selected from the group consisting of acetic acid, methanesulfonic acid, trifluoroacetic acid, and a sulfuric acid, and being present in an amount sufficient to accelerate the hydrogenation reaction but insufficient to cause the rearrangement of the arylhydroxylamine to an aminophenol.

18. The method of claim 14 wherein the protonic acid is selected from the class consisting of carboxylic acids, sulfonic acids, hydrogen halide acids and the oxoacids of phosphorus, nitrogen and sulfur.

* * * * *